United States Patent
Hyde et al.

(10) Patent No.: US 9,526,418 B2
(45) Date of Patent: Dec. 27, 2016

(54) DEVICE FOR STORAGE OF INTRALUMINALLY GENERATED POWER

(75) Inventors: Roderick A. Hyde, Redmond, WA (US); Muriel Y. Ishikawa, Livermore, CA (US); Eric C. Leuthardt, St. Louis, MO (US); Michael A. Smith, Phoenix, AZ (US); Lowell L. Wood, Jr., Bellevue, WA (US); Victoria Y. H. Wood, Livermore, CA (US)

(73) Assignee: Deep Science, LLC, Bellevue, WA (US)

( * ) Notice: Subject to any disclaimer, the term of this patent is extended or adjusted under 35 U.S.C. 154(b) by 1013 days.

(21) Appl. No.: 12/462,789

(22) Filed: Aug. 7, 2009

(65) Prior Publication Data
US 2010/0140943 A1    Jun. 10, 2010

Related U.S. Application Data

(63) Continuation-in-part of application No. 12/315,616, filed on Dec. 4, 2008, and a continuation-in-part of
(Continued)

(51) Int. Cl.

| | |
|---|---|
| *F02B 63/04* | (2006.01) |
| *F03G 7/08* | (2006.01) |
| *H02K 7/18* | (2006.01) |
| *A61B 5/00* | (2006.01) |
| *B60L 11/02* | (2006.01) |
| *B61C 9/38* | (2006.01) |

(52) U.S. Cl.
CPC .......... *A61B 5/00* (2013.01); *A61B 2560/0214* (2013.01)

(58) Field of Classification Search
USPC ................... 290/1 R, 10; 607/35; 600/16
See application file for complete search history.

(56) References Cited

U.S. PATENT DOCUMENTS 3,358,690 A * 12/1967 Cohen .............................. 607/23
3,421,512 A    1/1969 Frasier ............................ 607/35
(Continued)

FOREIGN PATENT DOCUMENTS

| EP | 1764034 | 3/2007 |
|---|---|---|
| GB | 1220677 | 1/1971 |
| GB | 2350302 | 11/2000 |

OTHER PUBLICATIONS

Lucklum, et al., Acoustic Wave Generation and Detection in Non-Piezoelectric High-Q Resonators, Ultrasonic Symposium 2006, Oct. 2006, pp. 1132-1135.
(Continued)

*Primary Examiner* — Tulsidas C Patel
*Assistant Examiner* — Pedro J Cuevas
(74) *Attorney, Agent, or Firm* — Faisal K. Abou-Nasr; Advent, LLP

(57) ABSTRACT

A device for storing power generated from intraluminal pressure changes may comprise: (a) an intraluminal pressure change-receiving structure operably coupled to the generator; (b) a intraluminal generator; and (c) an energy storage apparatus.
A system for storing power generated from intraluminal pressure changes may comprise: (a) means for receiving an intraluminal pressure change; (b) means for converting the intraluminal pressure change into energy with an intraluminal generator; and (c) means for storing the energy in an energy storage apparatus.

6 Claims, 13 Drawing Sheets

Related U.S. Application Data application No. 12/315,631, filed on Dec. 4, 2008, and a continuation-in-part of application No. 12/386,054, filed on Apr. 13, 2009, and a continuation-in-part of application No. 12/455,669, filed on Jun. 4, 2009, now Pat. No. 9,353,733, and a continuation-in-part of application No. 12/462,796, filed on Aug. 7, 2009.

(56) References Cited

U.S. PATENT DOCUMENTS

| | | | | |
|---|---|---|---|---|
| 3,456,134 | A | 7/1969 | Ko | 607/35 |
| 3,522,811 | A * | 8/1970 | Wingrove et al. | 607/27 |
| 3,563,245 | A * | 2/1971 | McLean et al. | 607/35 |
| 3,649,615 | A | 3/1972 | Ikeda et al. | 534/642 |
| 3,659,615 | A | 5/1972 | Enger | 607/35 |
| 3,861,397 | A * | 1/1975 | Rao et al. | 607/35 |
| 3,906,960 | A * | 9/1975 | Lehr | 607/35 |
| 3,943,936 | A | 3/1976 | Rasor et al. | 607/35 |
| 4,140,132 | A | 2/1979 | Dahl | 607/19 |
| 4,294,891 | A * | 10/1981 | Yao et al. | 429/2 |
| 4,453,537 | A * | 6/1984 | Spitzer | 623/3.12 |
| 4,538,616 | A | 9/1985 | Rogoff | 600/365 |
| 4,661,107 | A * | 4/1987 | Fink | 623/2.34 |
| 4,690,143 | A | 9/1987 | Schroeppel | 607/5 |
| 4,798,206 | A | 1/1989 | Maddison et al. | 607/122 |
| 5,007,927 | A * | 4/1991 | Badylak et al. | 623/3.12 |
| 5,010,893 | A | 4/1991 | Sholder | 600/595 |
| 5,022,395 | A | 6/1991 | Russie | 607/16 |
| 5,062,841 | A | 11/1991 | Siegel | 604/891.1 |
| 5,154,680 | A | 10/1992 | Drzewiecki et al. | 600/485 |
| 5,188,738 | A | 2/1993 | Kaali et al. | 424/529 |
| 5,205,286 | A | 4/1993 | Soukup et al. | 600/377 |
| 5,344,385 | A * | 9/1994 | Buck et al. | 600/16 |
| 5,348,019 | A | 9/1994 | Sluss, Jr. et al. | 600/480 |
| 5,363,855 | A | 11/1994 | Drzewiecki et al. | 600/485 |
| 5,366,454 | A | 11/1994 | Currie et al. | 604/890.1 |
| 5,411,537 | A * | 5/1995 | Munshi et al. | 607/33 |
| 5,431,694 | A | 7/1995 | Snaper et al. | 607/35 |
| 5,443,504 | A * | 8/1995 | Hill | 623/3.12 |
| 5,457,624 | A | 10/1995 | Hastings | 363/127 |
| 5,522,394 | A | 6/1996 | Zurbrugg | 600/459 |
| 5,535,752 | A | 7/1996 | Halperin et al. | 600/483 |
| 5,617,876 | A | 4/1997 | van Duyl | 600/595 |
| 5,626,141 | A | 5/1997 | Takeda | 600/490 |
| 5,653,676 | A * | 8/1997 | Buck et al. | 600/16 |
| 5,690,693 | A * | 11/1997 | Wang et al. | 607/61 |
| 5,693,952 | A | 12/1997 | Cox | 250/551 |
| 5,701,919 | A * | 12/1997 | Buck et al. | 128/898 |
| 5,702,431 | A * | 12/1997 | Wang et al. | 607/61 |
| 5,713,939 | A * | 2/1998 | Nedungadi et al. | 607/33 |
| 5,715,837 | A | 2/1998 | Chen | 128/899 |
| 5,734,564 | A | 3/1998 | Brkovic | 363/21.16 |
| 5,745,358 | A | 4/1998 | Faulk | 363/95 |
| 5,749,909 | A * | 5/1998 | Schroeppel et al. | 607/33 |
| 5,764,495 | A | 6/1998 | Faulk | 363/21.13 |
| 5,810,015 | A | 9/1998 | Flaherty | 128/897 |
| 5,823,199 | A | 10/1998 | Hastings et al. | 128/899 |
| 5,954,058 | A | 9/1999 | Flaherty | 128/899 |
| 5,967,986 | A | 10/1999 | Cimochowski et al. | 600/454 |
| 5,984,857 | A * | 11/1999 | Buck et al. | 600/16 |
| 6,164,284 | A | 12/2000 | Schulman et al. | 128/899 |
| 6,268,161 | B1 | 7/2001 | Han et al. | 435/14 |
| 6,291,900 | B1 * | 9/2001 | Tiemann et al. | 290/1 A |
| 6,409,674 | B1 | 6/2002 | Brockway et al. | 600/486 |
| 6,426,628 | B1 | 7/2002 | Palm et al. | 324/427 |
| 6,432,050 | B1 | 8/2002 | Porat et al. | 600/300 |
| 6,475,750 | B1 | 11/2002 | Han et al. | 435/14 |
| 6,524,256 | B2 | 2/2003 | Schaldach et al. | 600/486 |
| 6,564,807 | B1 | 5/2003 | Schulman et al. | 128/899 |
| 6,580,177 | B1 | 6/2003 | Hagood, IV et al. | 290/1 R |
| 6,589,184 | B2 | 7/2003 | Norén et al. | 600/486 |
| 6,635,048 | B1 | 10/2003 | Ullestad et al. | 604/890.1 |
| 6,638,231 | B2 | 10/2003 | Govari et al. | 600/486 |
| 6,682,490 | B2 | 1/2004 | Roy et al. | 600/486 |
| 6,711,423 | B2 | 3/2004 | Colvin, Jr. | 600/317 |
| 6,802,811 | B1 | 10/2004 | Slepian | 600/309 |
| 6,822,343 | B2 | 11/2004 | Estevez | 290/1 R |
| 6,827,682 | B2 | 12/2004 | Bugge et al. | 600/16 |
| 6,829,507 | B1 | 12/2004 | Lidman et al. | 607/19 |
| 6,860,857 | B2 | 3/2005 | Norén et al. | 600/486 |
| 6,895,265 | B2 | 5/2005 | Silver | 600/345 |
| 6,937,894 | B1 | 8/2005 | Isaac et al. | 607/5 |
| 6,953,469 | B2 | 10/2005 | Ryan | 606/192 |
| 7,032,600 | B2 | 4/2006 | Fukuda et al. | 128/899 |
| 7,033,322 | B2 | 4/2006 | Silver | 600/486 |
| 7,081,683 | B2 * | 7/2006 | Ariav | 290/1 R |
| 7,081,699 | B2 | 7/2006 | Keolian et al. | 310/311 |
| 7,167,756 | B1 | 1/2007 | Torgerson et al. | 607/61 |
| 7,223,237 | B2 | 5/2007 | Shelchuk | 600/309 |
| 7,241,266 | B2 | 7/2007 | Zhou et al. | 600/365 |
| 7,263,894 | B2 | 9/2007 | Tenerz | 73/756 |
| 7,302,856 | B2 | 12/2007 | Tang et al. | 73/777 |
| 7,362,557 | B2 | 4/2008 | Soudier et al. | 361/93.8 |
| 7,367,968 | B2 | 5/2008 | Rosenberg et al. | 604/891.1 |
| 7,403,821 | B2 | 7/2008 | Haugland et al. | 607/49 |
| 7,413,547 | B1 | 8/2008 | Lichtscheidl et al. | 600/486 |
| 7,424,325 | B2 | 9/2008 | Koller et al. | 607/35 |
| 7,425,200 | B2 | 9/2008 | Brockway et al. | 600/486 |
| 7,427,265 | B1 | 9/2008 | Keilman et al. | 600/300 |
| 7,452,334 | B2 | 11/2008 | Gianchandani et al. | 600/485 |
| 7,465,313 | B2 | 12/2008 | DiMauro et al. | 607/92 |
| 7,489,966 | B2 | 2/2009 | Leinders et al. | 607/2 |
| 7,616,990 | B2 | 11/2009 | Chavan et al. | 607/2 |
| 7,616,992 | B2 | 11/2009 | Dennis et al. | 607/9 |
| 7,715,918 | B2 * | 5/2010 | Melvin | 607/35 |
| 7,729,767 | B2 | 6/2010 | Baker, III et al. | 607/35 |
| 7,729,768 | B2 | 6/2010 | White et al. | 607/35 |
| 7,777,623 | B2 | 8/2010 | Albsmeier et al. | 340/539.26 |
| 7,798,973 | B2 | 9/2010 | Stahmann | 600/485 |
| 7,859,171 | B2 * | 12/2010 | Micallef | 310/339 |
| 2002/0028999 | A1 | 3/2002 | Schaldach et al. | 600/486 |
| 2003/0158584 | A1 | 8/2003 | Cates et al. | 607/2 |
| 2004/0021322 | A1 * | 2/2004 | Ariav | 290/1 R |
| 2004/0039242 | A1 * | 2/2004 | Tolkoff et al. | 600/9 |
| 2004/0078027 | A1 | 4/2004 | Shachar | 604/891.1 |
| 2004/0158294 | A1 * | 8/2004 | Thompson | 607/17 |
| 2004/0173220 | A1 | 9/2004 | Harry et al. | 128/892 |
| 2004/0193058 | A1 | 9/2004 | Montegrande et al. | 600/488 |
| 2004/0204744 | A1 | 10/2004 | Penner et al. | 607/23 |
| 2004/0215279 | A1 | 10/2004 | Houben et al. | 607/35 |
| 2005/0055061 | A1 * | 3/2005 | Holzer | 607/35 |
| 2005/0080346 | A1 | 4/2005 | Gianchandani et al. | 600/486 |
| 2005/0256549 | A1 | 11/2005 | Holzer | 607/35 |
| 2005/0261563 | A1 | 11/2005 | Zhou et al. | 600/347 |
| 2006/0044078 | A1 | 3/2006 | Ayazi et al. | 333/186 |
| 2006/0152309 | A1 | 7/2006 | Mintchev et al. | 335/58 |
| 2006/0184206 | A1 * | 8/2006 | Baker et al. | 607/35 |
| 2006/0217776 | A1 * | 9/2006 | White et al. | 607/35 |
| 2006/0224214 | A1 * | 10/2006 | Koller et al. | 607/62 |
| 2006/0247724 | A1 | 11/2006 | Gerber et al. | 607/41 |
| 2006/0287598 | A1 | 12/2006 | Lasater et al. | 600/439 |
| 2007/0074731 | A1 * | 4/2007 | Potter | 128/899 |
| 2007/0088402 | A1 * | 4/2007 | Melvin | 607/35 |
| 2007/0093875 | A1 | 4/2007 | Chavan et al. | 607/46 |
| 2007/0142728 | A1 | 6/2007 | Penner et al. | 600/486 |
| 2007/0149885 | A1 | 6/2007 | Corl et al. | 600/505 |
| 2007/0167776 | A1 | 7/2007 | Cernasov | 607/35 |
| 2007/0221233 | A1 | 9/2007 | Kawano et al. | 128/899 |
| 2007/0293904 | A1 * | 12/2007 | Gelbart et al. | 607/35 |
| 2008/0009687 | A1 | 1/2008 | Smith et al. | 600/302 |
| 2008/0021333 | A1 | 1/2008 | Huelskamp | 600/486 |
| 2008/0082005 | A1 | 4/2008 | Stern et al. | 600/486 |
| 2008/0132967 | A1 | 6/2008 | Von Arx et al. | 607/18 |
| 2008/0172043 | A1 | 7/2008 | Sheppard et al. | 604/891.1 |
| 2008/0212262 | A1 * | 9/2008 | Micallef | 361/502 |
| 2008/0262562 | A1 * | 10/2008 | Roberts et al. | 607/35 |
| 2008/0281298 | A1 | 11/2008 | Andersen et al. | 604/891.1 |
| 2009/0171413 | A1 | 7/2009 | Zenati et al. | 607/32 |
| 2009/0171448 | A1 | 7/2009 | Eli | 623/1.32 |
| 2009/0270742 | A1 | 10/2009 | Wolinsky et al. | 600/486 |
| 2009/0281399 | A1 | 11/2009 | Keel et al. | 600/301 |
| 2009/0292335 | A1 * | 11/2009 | Leonov | 607/35 |
| 2010/0010600 | A1 | 1/2010 | Eriksson et al. | 607/116 |
| 2010/0030043 | A1 | 2/2010 | Kuhn | 600/339 |

(56) References Cited

U.S. PATENT DOCUMENTS

| | | | |
|---|---|---|---|
| 2010/0036450 A1 | 2/2010 | Axelrod et al. | 607/35 |
| 2010/0049275 A1 | 2/2010 | Chavan et al. | 607/44 |
| 2010/0076517 A1* | 3/2010 | Imran | 607/35 |
| 2010/0140943 A1 | 6/2010 | Hyde et al. | 290/50 |
| 2010/0140956 A1 | 6/2010 | Hyde et al. | 290/1 R |
| 2010/0140957 A1 | 6/2010 | Hyde et al. | 290/1 R |
| 2010/0140958 A1 | 6/2010 | Hyde et al. | 290/1 R |
| 2010/0140959 A1 | 6/2010 | Hyde et al. | 290/1 R |
| 2010/0141052 A1 | 6/2010 | Hyde et al. | 307/151 |
| 2010/0228312 A1* | 9/2010 | White et al. | 607/35 |
| 2010/0298720 A1* | 11/2010 | Potkay | 600/485 |
| 2011/0062713 A1 | 3/2011 | Ardoise et al. | 290/53 |
| 2011/0094314 A1 | 4/2011 | Dekker et al. | 73/862.045 |
| 2011/0275947 A1 | 11/2011 | Feldman et al. | 600/508 |

OTHER PUBLICATIONS

Franklin Hadley, Goodbye Wires . . . MIT team experimentally demonstrates wireless power transfer, potentially useful for powering laptops, cell phones without cords; MIT News, Jun. 7, 2007, Publisher: http://web.mit.edu/newsoffice/2007/wireless-0607.html, Published in: US.

Chaimanonart, et al., Implantable RF Power Converter for Small Animal in Vivo Biological Monitoring, Sep. 1-4, 2005, Publisher: Proceedings of the 2005 IEEE Engineering in Medicine and Biology 27th Annual Conference.

Zhong Lin Wang, Self-Powered Nanotech: Nanosize Machines Need Still Tinier Power Plants, Scientific American Magazine, Dec. 16, 2007, pp. 82-87, Published in: US.

Dmitriev, et al., Tunable High-Q Surface-Acoustic-Wave Resonator, http://www.ingentaconnect.com/content/maok/10637842/2007/00000052/ . . . , Aug. 2007, pp. 1061-1067, vol. 52, No. 8, Publisher: Maik Naukal Interperiodica.

Kara Gavin, Zapping the Heart Back Into Rhythm, University of Michigan Health Minute, Jun. 2, 2005, Published in: Ann Arbor, MI.

Dmitriev, V.F., et al., "Tunable High-Q Surface-Acoustic-Wave Resonator"; Technical Physics, vol. 52, No. 8, Aug. 2007, pp. 1061-1067.

Lucklum, Frieder, et al., "Acoustic Wave Generation and Detection in Non-Piezoelectric High-Q Resonators", Ultrasonics Symposium, 2006, Oct. 2006, pp. 1132-1135.

\* cited by examiner

DEVICE FOR STORAGE OF INTRALUMINALLY GENERATED POWER

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 12/315,631, titled "Method for Generation of Power from Intraluminal Pressure Changes," naming Roderick A. Hyde, Muriel Y. Ishikawa, Eric C. Leuthardt, Michael A. Smith, Lowell L. Wood, Jr. and Victoria Y. H. Wood as inventors, filed Dec. 4, 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/315,616, titled "Method for Generation of Power from Intraluminal Pressure Changes", naming Roderick A. Hyde, Muriel Y. Ishikawa, Eric C. Leuthardt, Michael A. Smith, Lowell L. Wood, Jr. and Victoria Y. H. Wood as inventors, filed Dec. 4, 2008, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/386,054, titled "Method for Generation of Power from Intraluminal Pressure Changes", naming Roderick A. Hyde, Muriel Y. Ishikawa, Eric C. Leuthardt, Michael A. Smith, Lowell L. Wood, Jr. and Victoria Y. H. Wood as inventors, filed Apr. 13, 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/455,699, titled "Device and System for Generation of Power from Intraluminal Pressure Changes", naming Roderick A. Hyde, Muriel Y. Ishikawa, Eric C. Leuthardt, Michael A. Smith, Lowell L. Wood, Jr. and Victoria Y. H. Wood as inventors, filed Jun. 4, 2009, now U.S. Pat. No. 9,353,733, or is an application of which a currently co-pending application is entitled to the benefit of the filing date.

For purposes of the USPTO extra-statutory requirements, the present application constitutes a continuation-in-part of the Patent Application associated with U.S. patent application Ser. No. 12/462,796, titled "System for Powering Devices from Intraluminal Pressure Changes", naming Roderick A. Hyde, Muriel Y. Ishikawa, Eric C. Leuthardt, Michael A. Smith, Lowell L. Wood, Jr. and Victoria Y. H. Wood as inventors, filed Aug. 7, 2009, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BACKGROUND

Small scale generators for generating energy at levels suitable for powering devices which are in vivo or ex vivo to a human or animal are described. Such generators may be implanted in luminal structures so as to extract power from intraluminal pressure changes.

DETAILED DESCRIPTION

Figure 1:
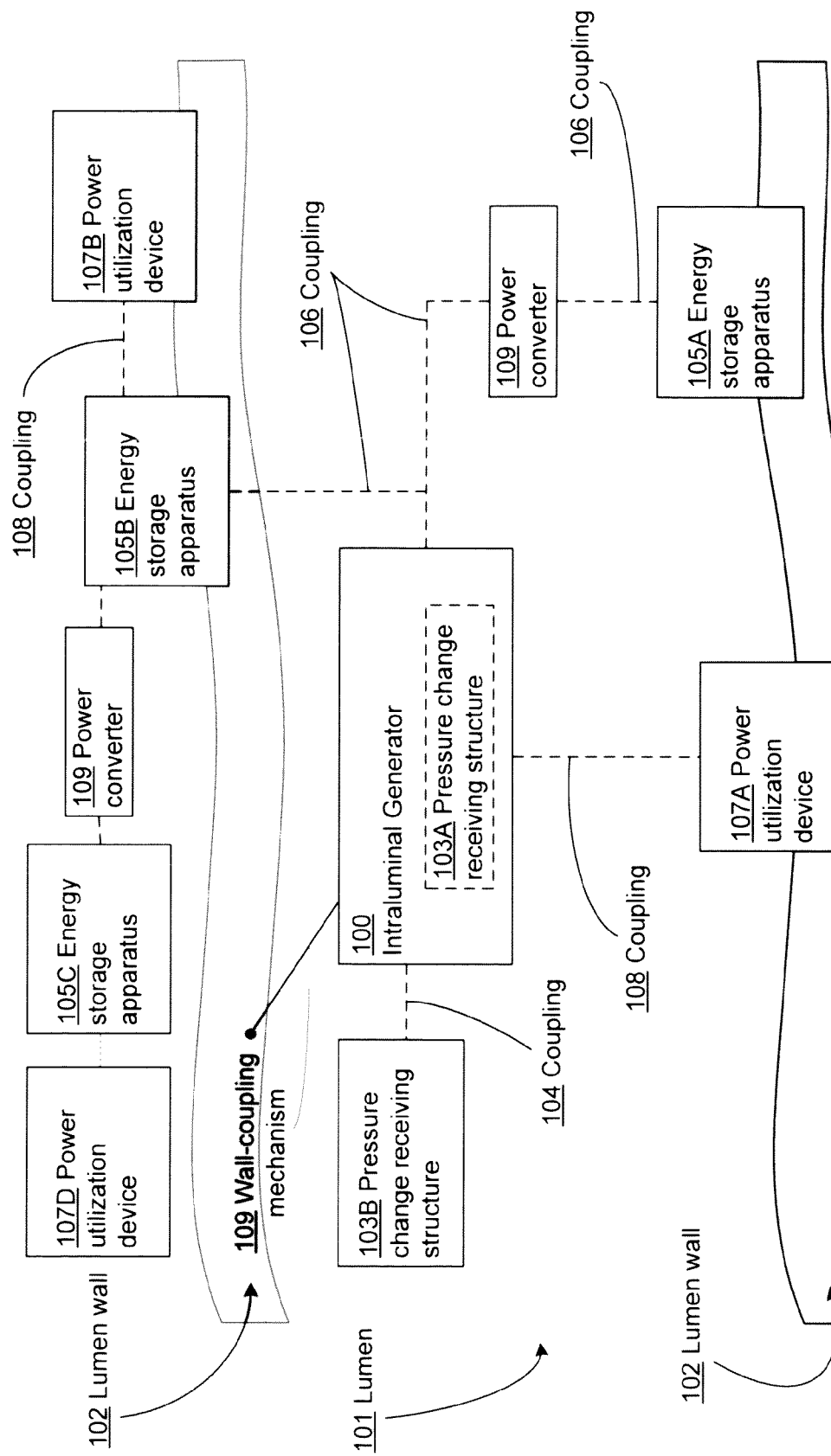
FIG. 1 shows a high-level block diagram of an intraluminal power generation device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Figure 2:
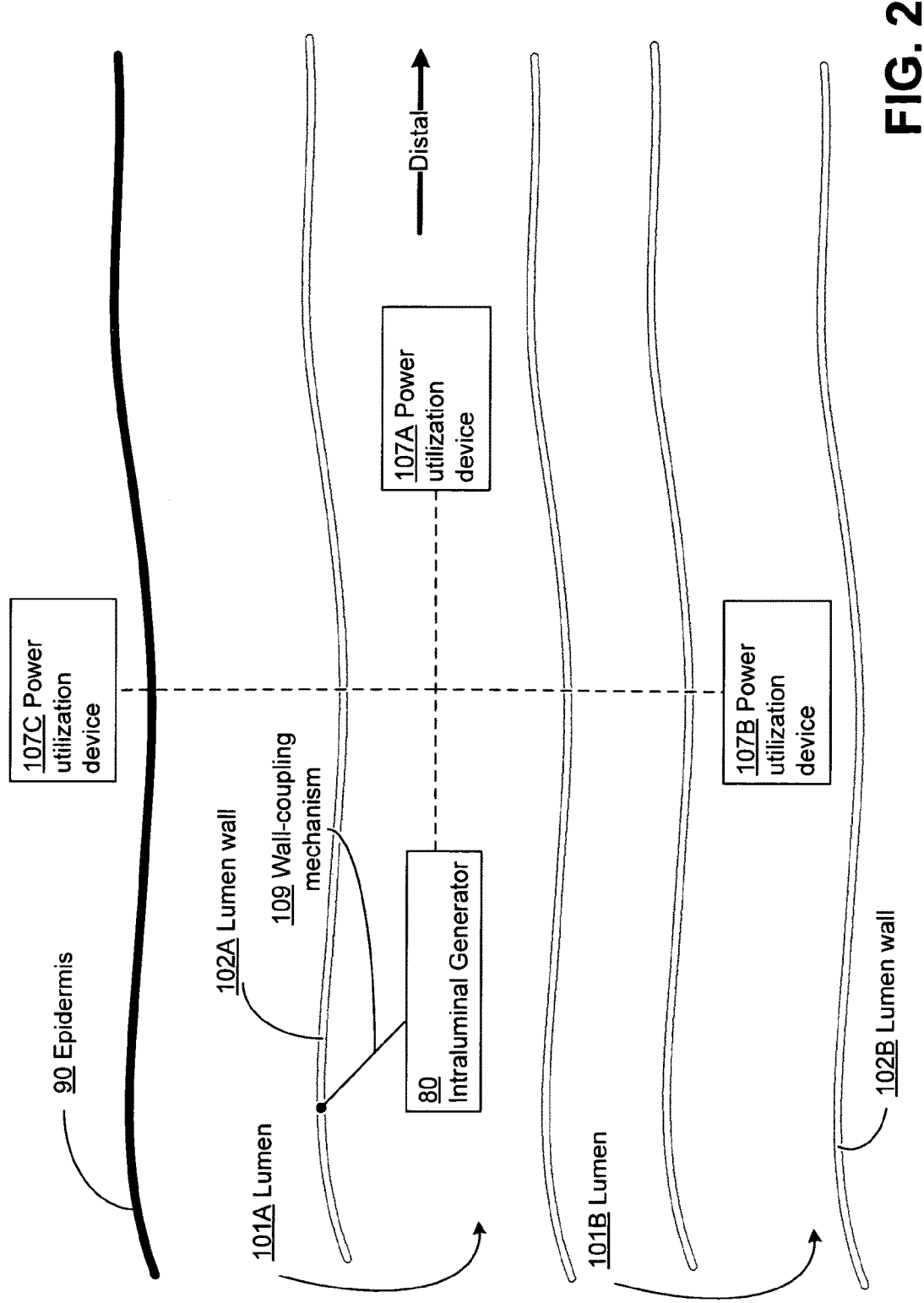
FIG. 2 shows a high-level block diagram of an intraluminal power generation device.
Figure 3:
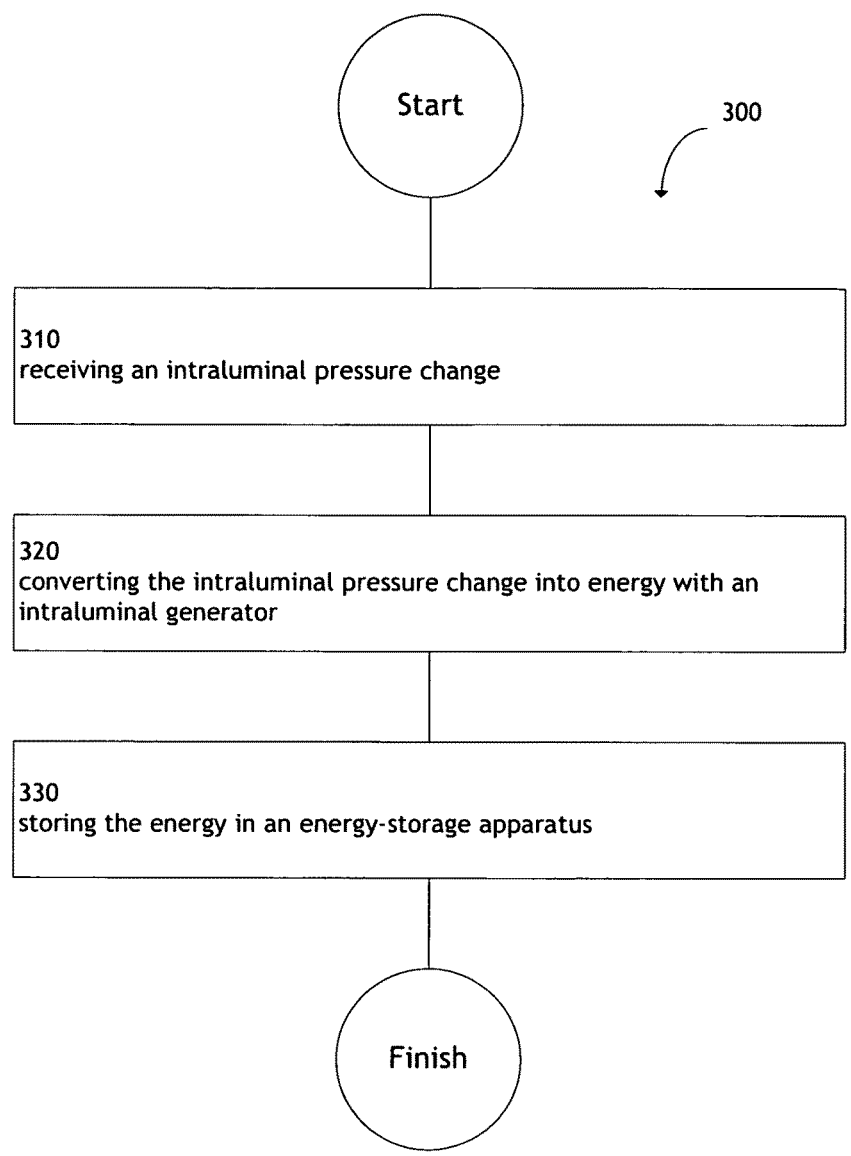
FIG. 3 shows a process for storage of intraluminally generated power.
Figure 4:
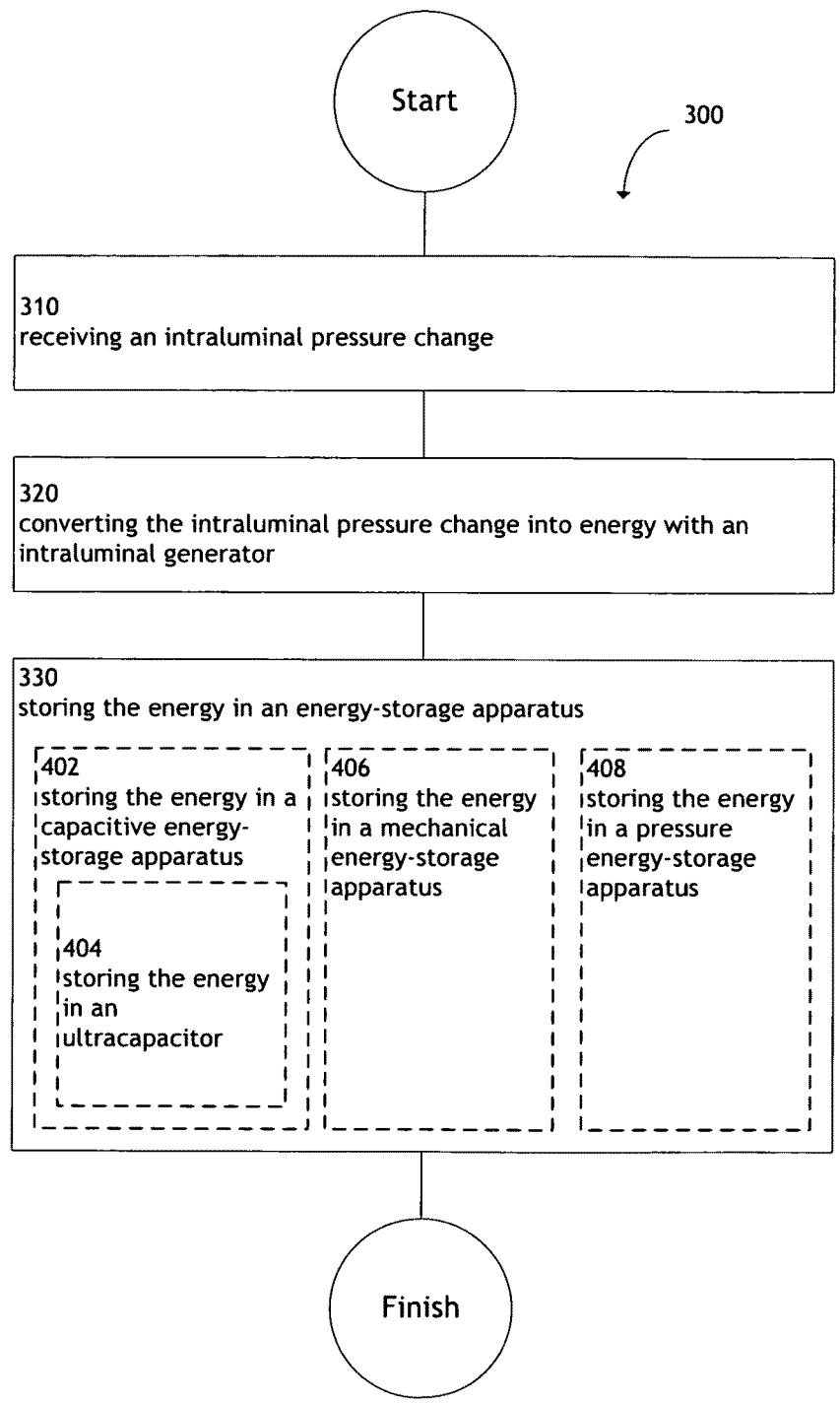
FIG. 4 shows a process for storage of intraluminally generated power.
Figure 5:
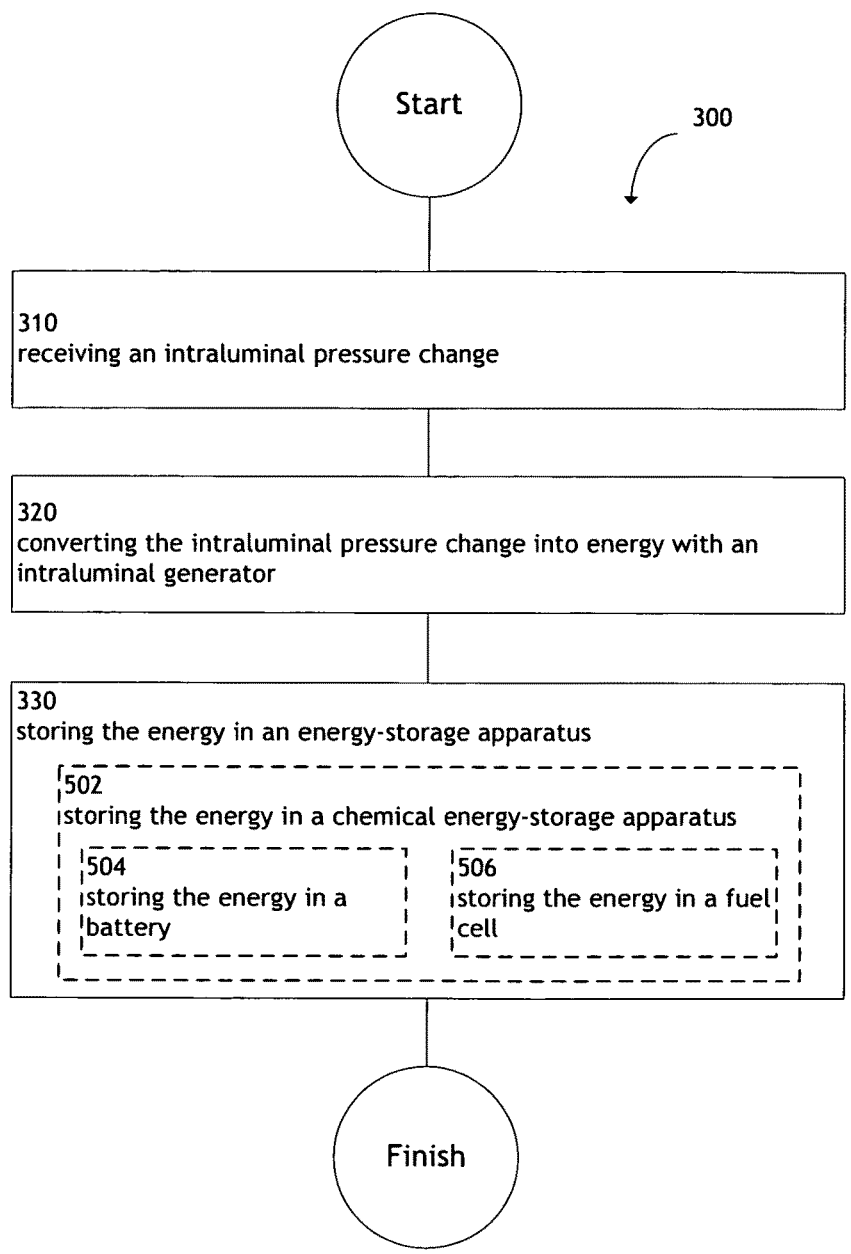
FIG. 5 shows a process for storage of intraluminally generated power.
Figure 6:
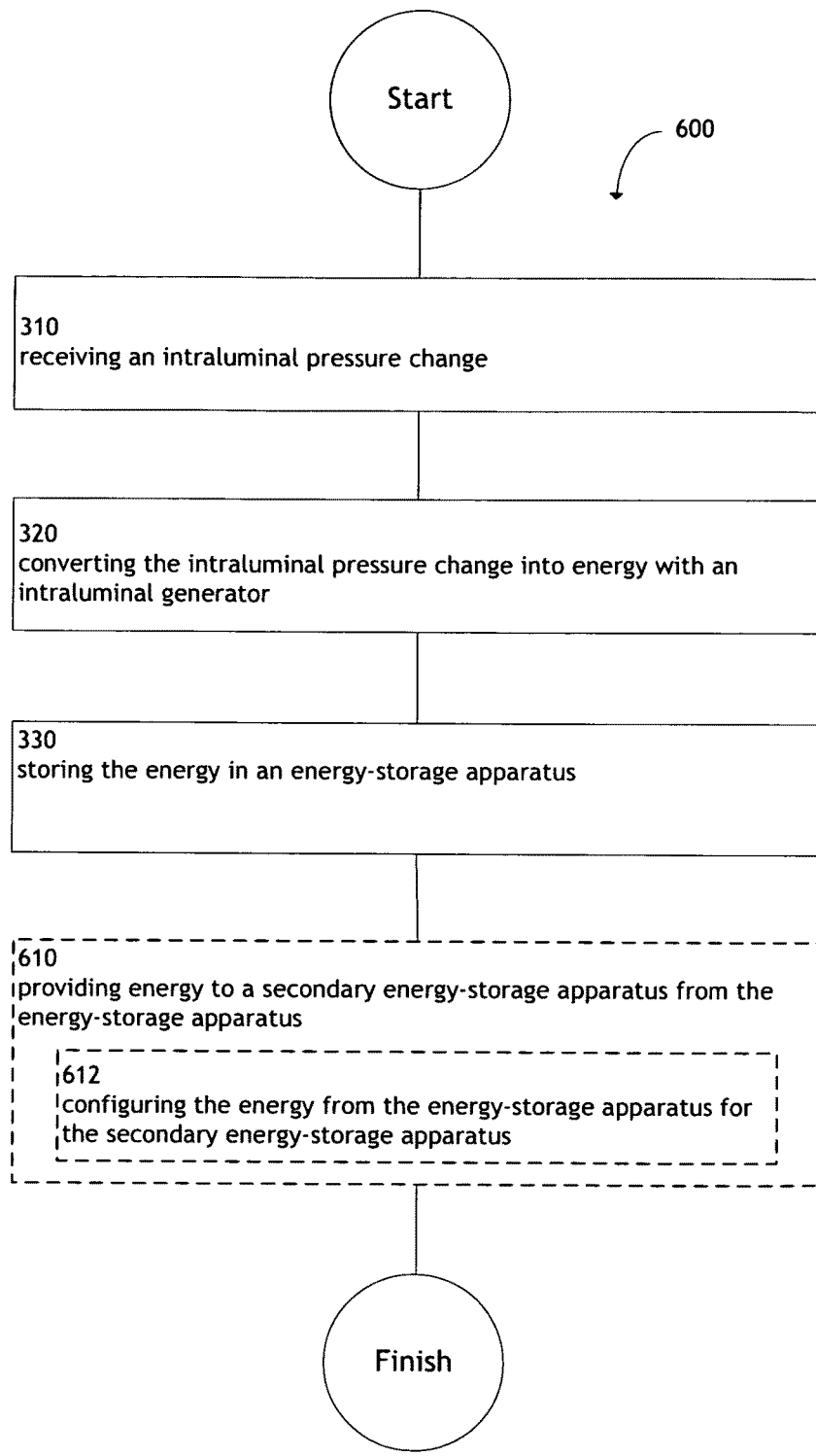
FIG. 6 shows a process for storage of intraluminally generated power.
Figure 7:
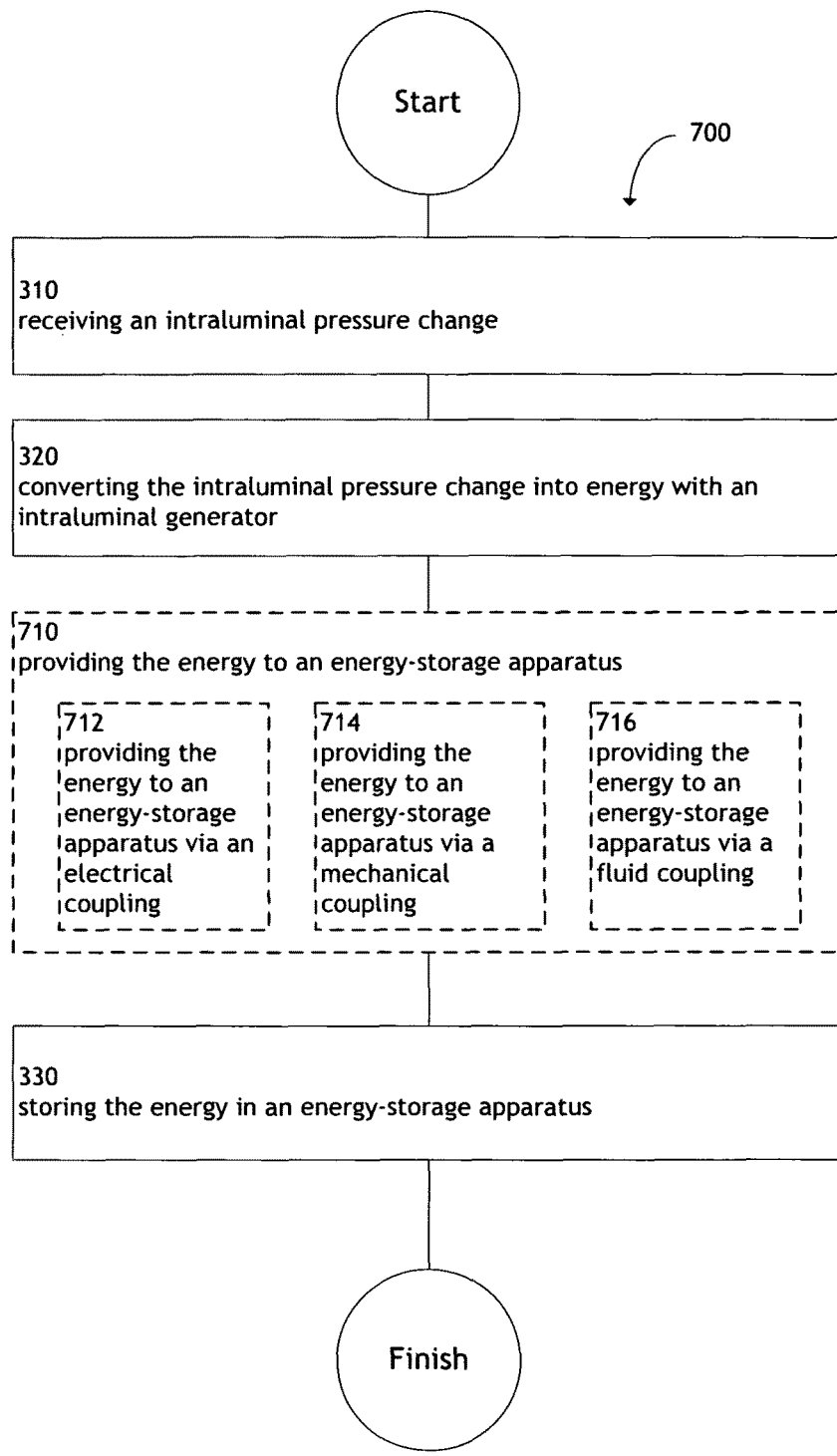
FIG. 7 shows a process for storage of intraluminally generated power.
Figure 8:
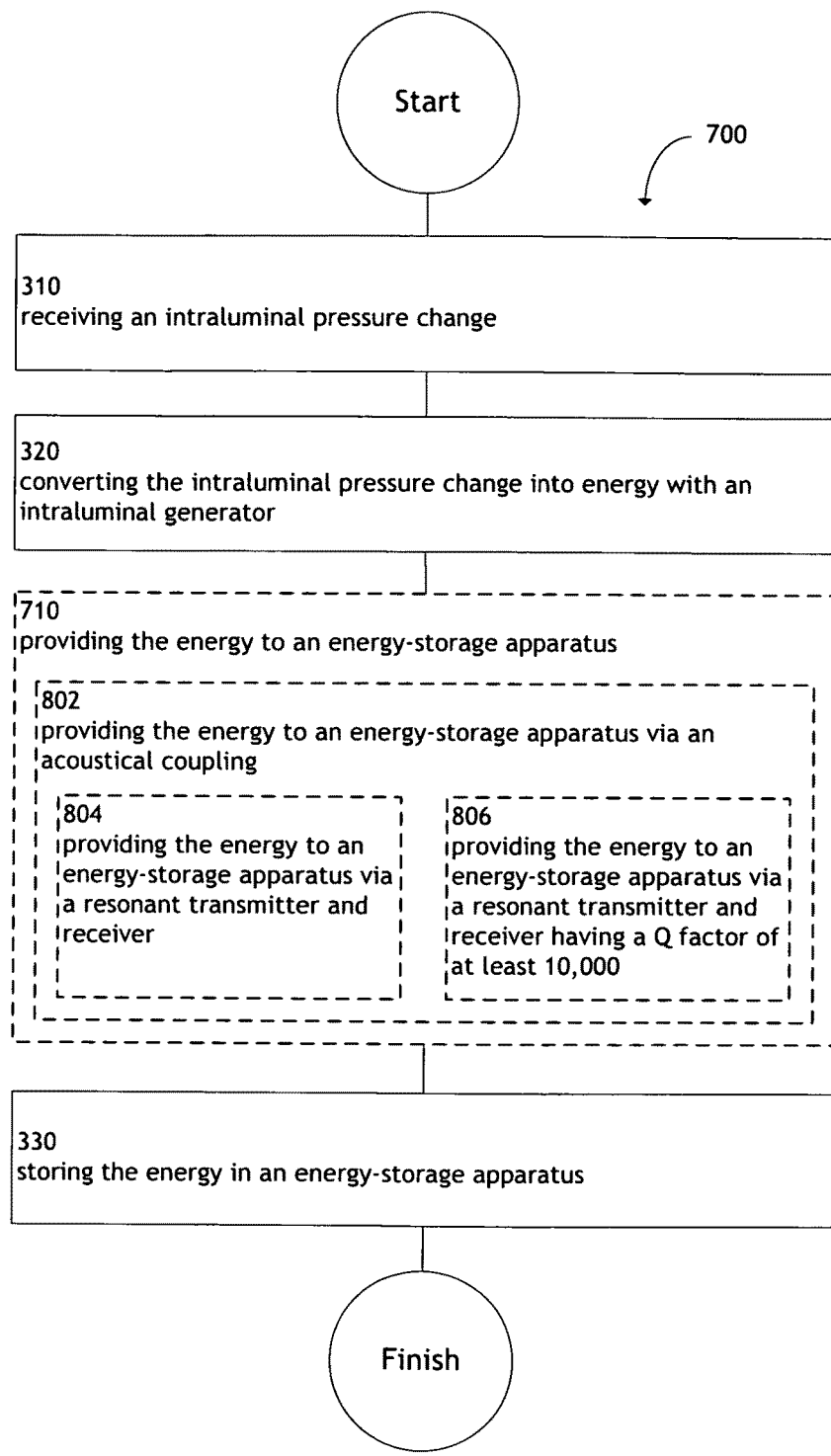
FIG. 8 shows a process for storage of intraluminally generated power.
Figure 9:
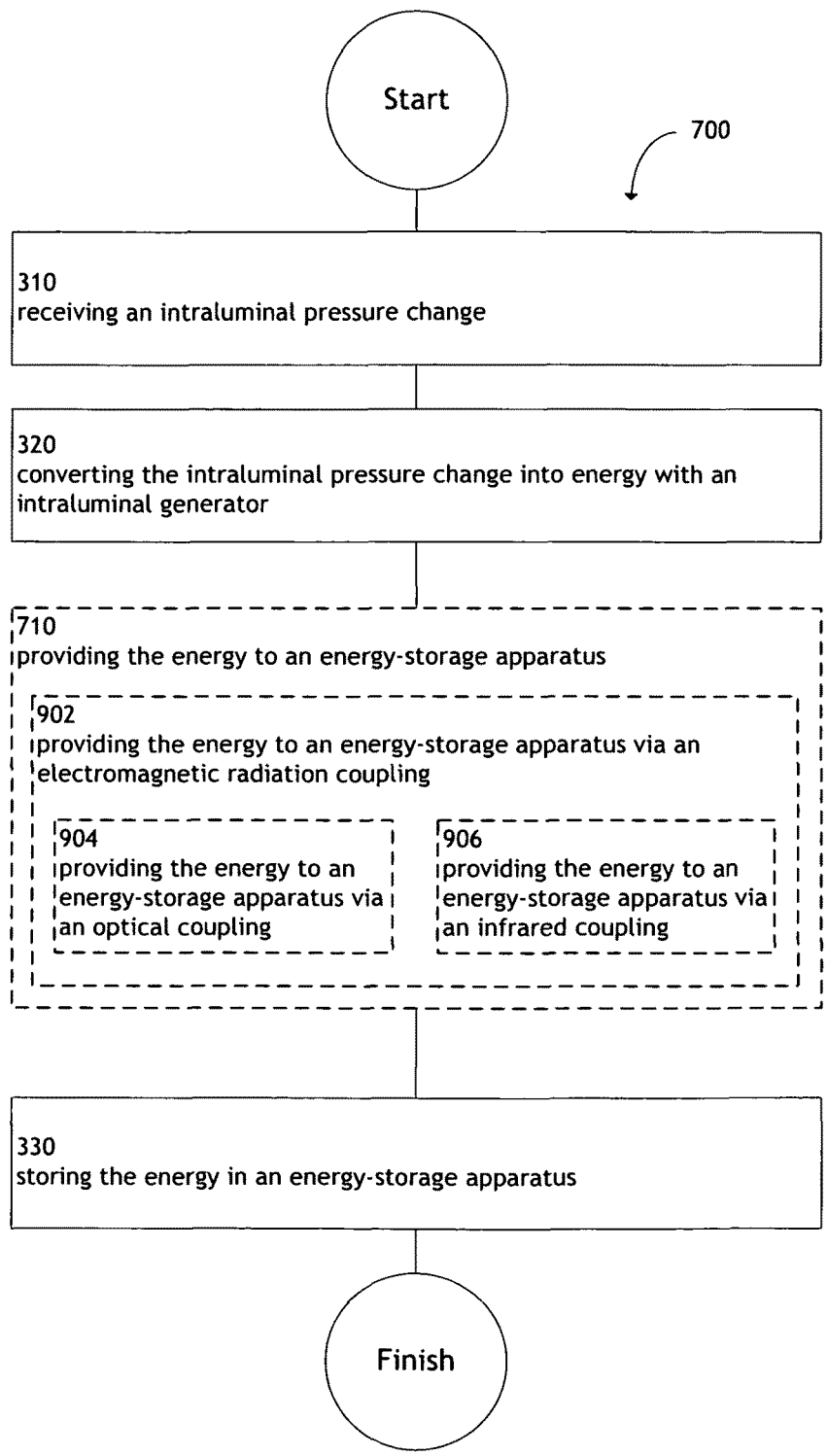
FIG. 9 shows a process for storage of intraluminally generated power.
Figure 10:
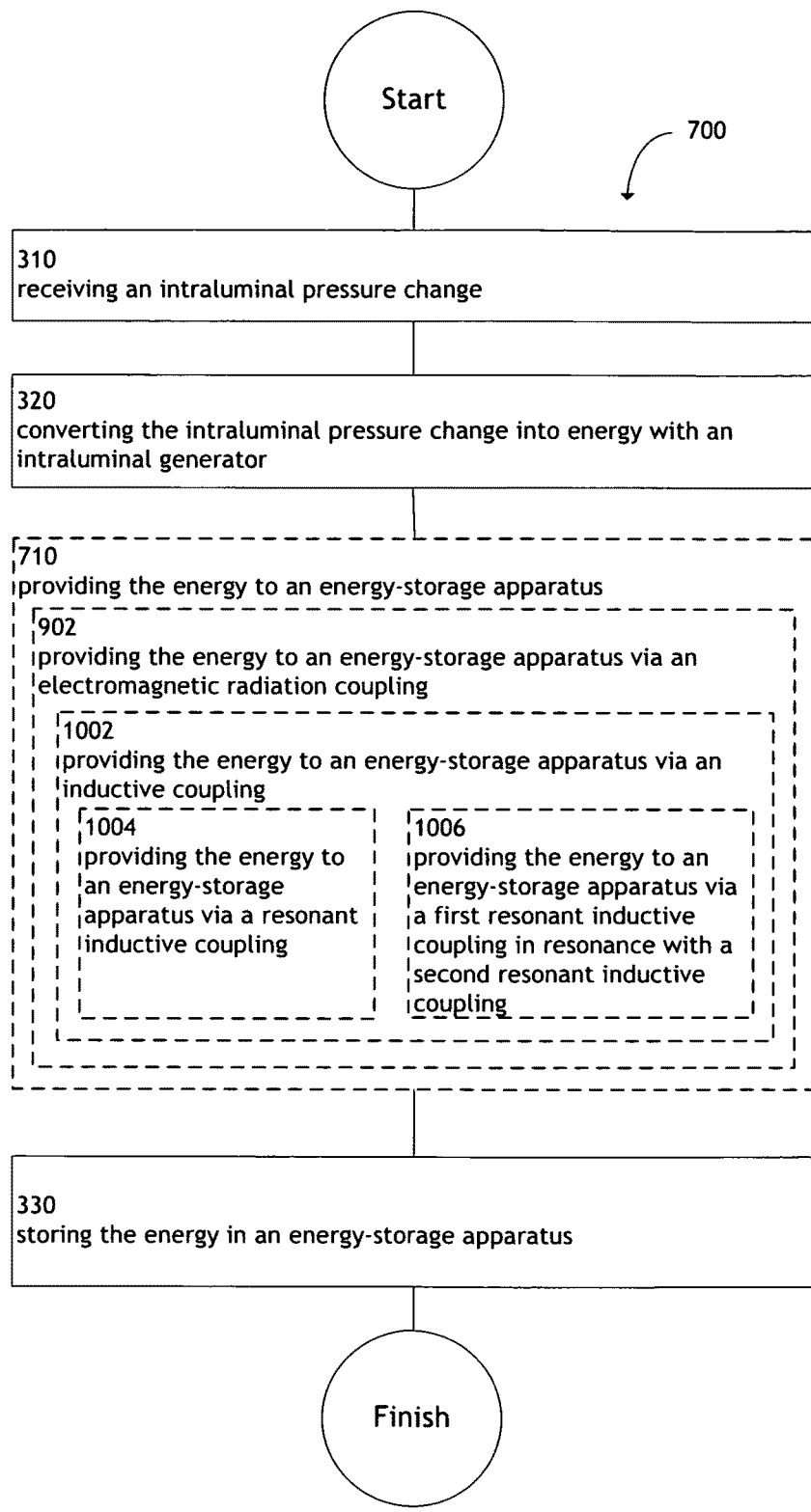
FIG. 10 shows a process for storage of intraluminally generated power.
Figure 11:
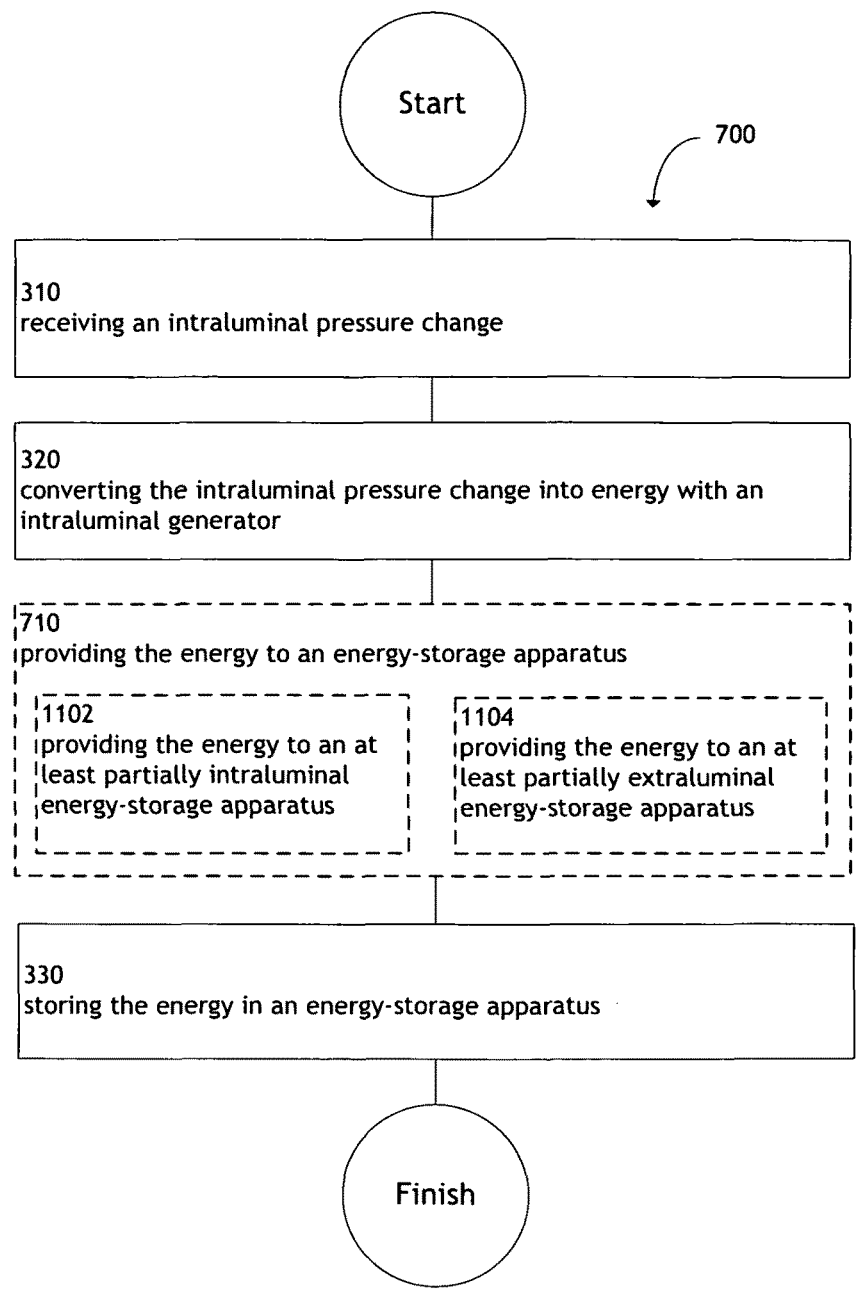
FIG. 11 shows a process for storage of intraluminally generated power.
Figure 12:
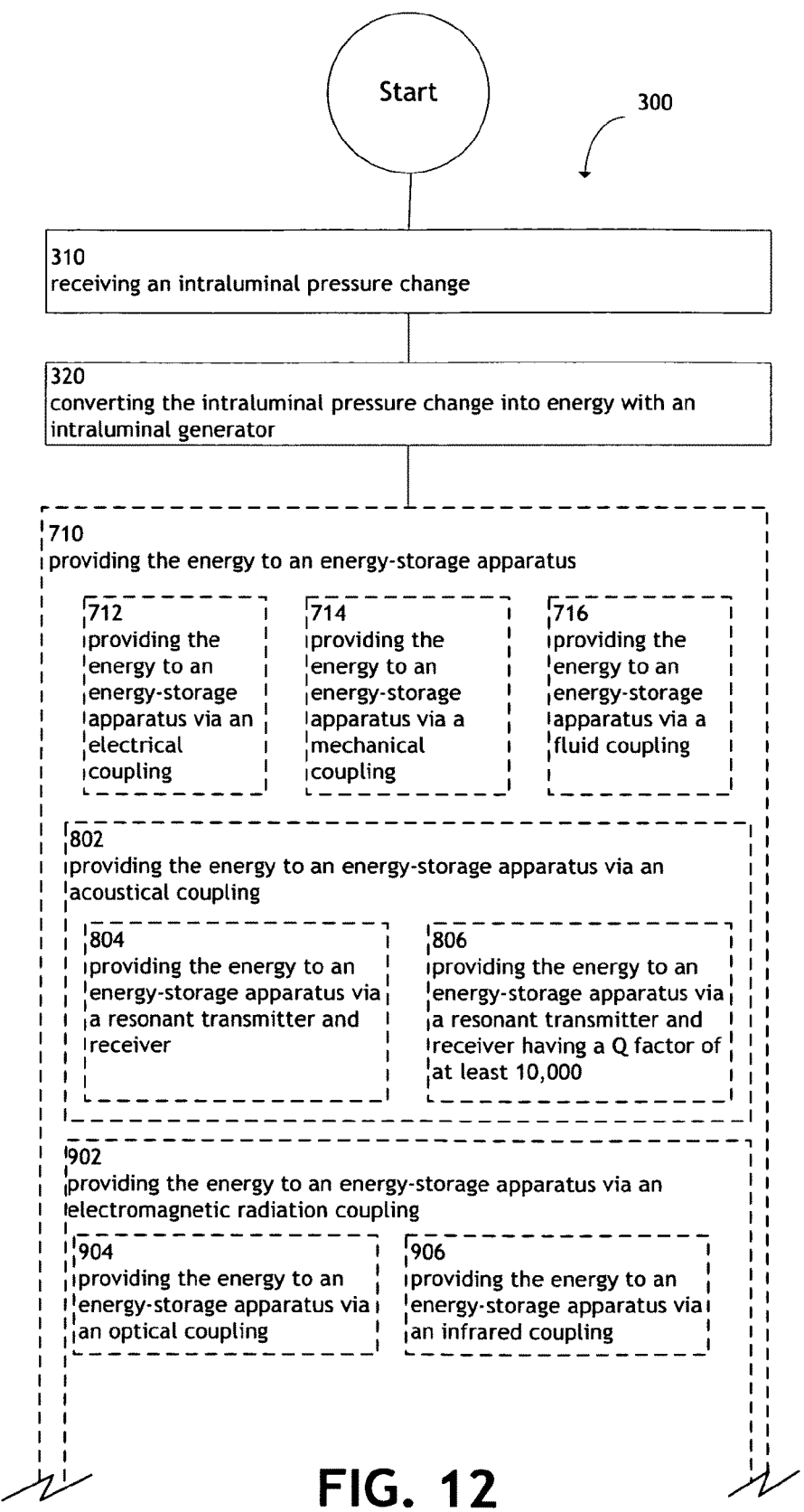
FIG. 12 shows a process for storage of intraluminally generated power.
Figure 12:
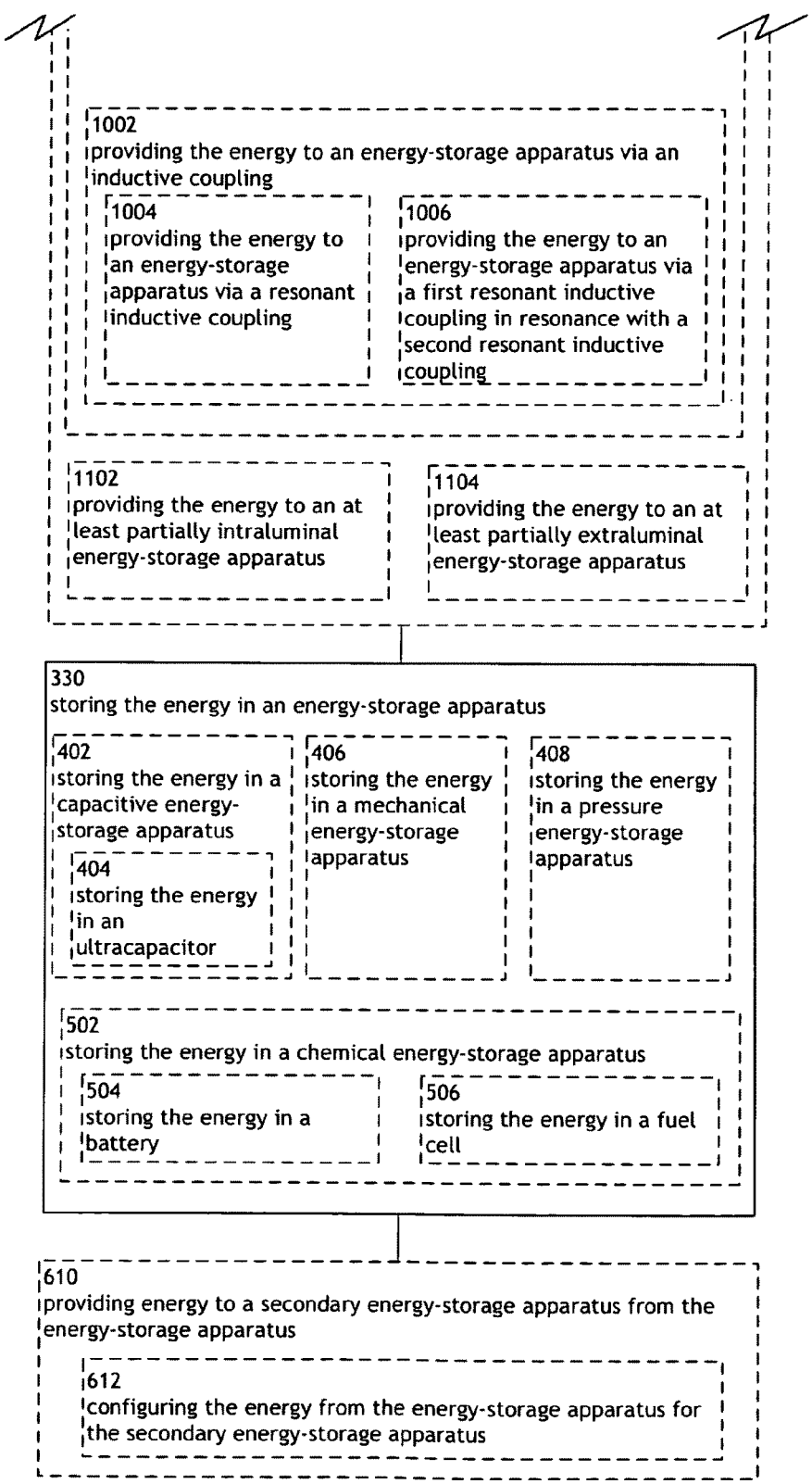

FIGS. 1 and 2 illustrate example environments in which one or more technologies may be implemented. An intraluminal power generation device may comprise intraluminal generator 100 configured for disposal within an anatomical lumen 101 defined by a lumen wall 102. The intraluminal generator 100 may be configured to convert a varying intraluminal pressure into energy (e.g. electrical energy, mechanical/elastic energy, chemical energy, thermal energy).

The intraluminal generator 100 may include an integrated pressure change receiving structure 103A configured to receive a pressure change associated with a fluid pressure within the lumen 101. Alternately, the pressure change receiving structure 103 may be an external pressure change receiving structure 103B operably coupled to the intraluminal generator 100 via a coupling 104 to transfer a received pressure from the pressure change receiving structure 103B to the intraluminal generator 100 in a form which the intraluminal generator 100 may convert to energy.

The intraluminal power generation device may comprise an energy storage apparatus 105 for storage of energy generated by the intraluminal generator 100. The energy storage apparatus 105 may be operably coupled to the intraluminal generator 100 by a coupling 106.

The intraluminal power generation device may comprise a power utilization device 107 that may use energy generated by the intraluminal generator 100 and/or stored in the energy storage apparatus 105 to carry out a desired function. The power utilization device 107 may be operably coupled to the intraluminal generator 100 and/or an energy storage apparatus 105 by a coupling 108.

FIG. 2 illustrates various configurations of one or more components of an intraluminal power generation device. The intraluminal generator 100 may be operably coupled to power utilization device 107A disposed in a first lumen 101A (e.g. in a distal relationship to the power utilization device 107A). An intraluminal generator 100 disposed within in a first lumen 101A may be operably coupled to power utilization device 107B disposed in a second lumen 101B. An intraluminal generator 100 disposed within in a first lumen 101A may be operably coupled to an ex vivo power utilization device 107C disposed outside an epidermis layer.

Referring to FIGS. 1-3 and 12, the intraluminal generator 100 may be a intraluminal generator. For example, as shown in FIG. 1, the intraluminal generator 100 may be disposed (e.g. surgically implanted) within in a lumen 101. The intraluminal generator 100 may be coupled to the wall of the lumen 101 to maintain the intraluminal generator 100 in place. The intraluminal generator 100 may comprise biocompatible materials (e.g. ultra high molecular weight polyethylene, polysulfone, polypropylene, titanium, and the like) such that the intraluminal generator 100 may be suitable for disposal within the lumen 101. The exterior surface of the intraluminal generator 100 may be configured such that the flow characteristics of a fluid moving through the lumen 101 are substantially maintained (e.g. the flow rate of the fluid, the flow dynamics of the fluid, and the like are not substantially disrupted.) The intraluminal generator 100 may be a stent-type structure.

A movement and/or deformation of the pressure change receiving structure 103 may be translated either directly (e.g. the intraluminal generator 100 comprises the pressure change receiving structure 103A) or indirectly (e.g. the pressure change receiving structure 103B is operably coupled to a generator) into energy either through the motion of the pressure change receiving structure 103 and/or the electrical properties of the materials comprising the pressure change receiving structure 103.

Referring to FIGS. 1-3 and 12, a change in pressure within the lumen 101 may be received by a pressure change receiving structure 103. The pressure change receiving structure 103 may receive a change in pressure through exposure of a surface of the pressure change receiving structure 103 to the luminal environment such that a change in the intraluminal pressure may exert a force on the pressure change receiving structure 103 thereby resulting in a movement and/or deformation of the pressure change receiving structure 103.

Referring to FIGS. 1-3 and 12, a movement and/or deformation of the pressure change receiving structure 103 may be translated either directly (e.g. the intraluminal generator 100 comprises the pressure change receiving structure 103A) or indirectly (e.g. the pressure change receiving structure 103B is operably coupled to a generator) into energy either through the motion of the pressure change receiving structure 103 and/or the electrical properties of the materials comprising the pressure change receiving structure 103 and/or the intraluminal generator 100.

Referring to FIGS. 1-3 and 12, energy generated by the intraluminal generator 100 in response to the movement and/or deformation of the pressure change receiving structure 103 may be stored in an energy storage apparatus 105. The energy storage apparatus 105 may be configured to store one or more forms of energy. For example, the energy storage apparatus 105 may be a chemical energy storage apparatus, an electrical energy storage apparatus, a mechanical energy storage apparatus, and the like.

Referring to FIGS. 1-2, 4 and 12, energy generated by the intraluminal generator 100 in response to the movement and/or deformation of the pressure change receiving structure 103 may be stored in a capacitive energy storage apparatus 105. A capacitive energy storage apparatus 105 may comprise two conducting electrodes separated by a dielectric. The capacitive energy storage apparatus 105 may be electrolytic or electrostatic.

Referring to FIGS. 1-2, 4 and 12, energy generated by the intraluminal generator 100 in response to the movement and/or deformation of the pressure change receiving structure 103 may be stored in an ultracapacitive energy storage apparatus 105. An ultracapacitive energy storage apparatus 105 may be an electric double-layer capacitor comprising two or more dielectric layers. The dielectric layers may comprise activated carbon, carbon nanotubes, activated polypyrrole, barium titanate, and the like.

Referring to FIGS. 1-2, 4 and 12, energy generated by the intraluminal generator 100 in response to the movement and/or deformation of the pressure change receiving structure 103 may be stored in a mechanical energy storage apparatus 105. The intraluminal generator 100 may include a mechanical linkage (e.g. a lever mechanism) operably coupled to a mechanical energy storage apparatus 105 whereby movement of the mechanical linkage in response to the movement and/or deformation of the pressure change receiving structure 103 may cause the mechanical energy storage apparatus 105 to store a mechanical energy (e.g. as a spring force, kinetic energy, and the like). The mechanical energy storage apparatus 105 may include a spring and ratchet, a flywheel, and the like.

Referring to FIGS. 1-2, 4 and 12, energy generated by the intraluminal generator 100 in response to the movement and/or deformation of the pressure change receiving structure 103 may be stored in a pressure energy storage apparatus 105. The intraluminal generator 100 may include a pump mechanism operably coupled to a pressure energy storage apparatus 105 whereby movement and/or deformation of the pressure change receiving structure 103 may cause the pressure energy storage apparatus 105 to store pressure energy. The mechanical energy storage apparatus 105 may include a rigid, semi-rigid or elastic pressure vessel.

Referring to FIGS. 1-2, 5 and 12, energy generated by the intraluminal generator 100 in response to the movement and/or deformation of the pressure change receiving structure 103 may be stored in a chemical energy storage apparatus 105. The chemical energy storage apparatus 105 may include one or more electrochemical cells such as of a galvanic cell, an electrolytic cell, a fuel cell, a flow cell, a voltaic pile and the like.

A chemical energy storage apparatus 105 may comprise a battery. The battery may comprise one or more voltaic cells. The battery may be a rechargeable battery such as a nickel cadmium (NiCd), nickel metal hydride (NiMH), lithium ion (Li-ion), and lithium ion polymer (Li-ion polymer) which may be charged by energy produced by the intraluminal generator 100.

A chemical energy storage apparatus 105 may comprise a fuel cell. The fuel cell may be selected from one or more of a metal hydride fuel cell, an electro-galvanic fuel cell, a direct formic acid fuel cell (DFAFC), a zinc-air fuel cell, a microbial fuel cell, an upflow microbial fuel cell (UMFC), a direct borohydride fuel cell, an alkaline fuel cell, a direct methanol fuel cell, a reformed methanol fuel cell, a direct formic acid fuel cell, proton exchange membrane fuel cell, an RFC—Redox fuel cell, a protonic ceramic fuel cell, a direct carbon fuel cell, a planar solid oxide fuel cell, and the like. The fuel cell may be a reversible fuel cell combined with an electrolyzer and a fuel storage apparatus to utilize an electrical current generated by the intraluminal generator 100 to generate fuel cell fuel components (e.g. oxygen and hydrogen) from a fuel cell product (e.g. water). The fuel cell fuel components may be stored in a fuel cell storage apparatus for later use in recovering energy from the fuel cell fuel components via the fuel cell.

Referring to FIGS. 1-2, 6 and 12, energy stored in the energy storage apparatus 105B may be transmitted to a secondary energy storage apparatus 105C from the energy storage apparatus 105B.

Referring to FIGS. 1-2, 6 and 12, energy transmitted from the energy storage apparatus 105B to the secondary energy storage apparatus 105C may be configured by a power converter. For example, as shown in FIG. 1, energy stored in energy storage apparatus 105B may be configured by a power converter 109 prior to storage in a secondary energy storage apparatus 105C. The energy stored in the energy storage apparatus 105B may be unsuitable for use by a particular power utilization device 107D. As such, the energy stored in the energy storage apparatus 105B may be configured (e.g. voltage regulation, current regulation, inversion, rectification, phase modification, translation into another form of energy (e.g. converting electrical energy to mechanical energy) and the like) and stored in secondary energy storage apparatus 105C for use by power utilization device 107D.

Referring to FIGS. 1-2, 7 and 12, energy generated by the intraluminal generator 100 in response to the movement and/or deformation of the pressure change receiving structure 103 may be transmitted to an energy storage apparatus 105 operably coupled to the intraluminal generator 100 by a coupling 106.

Referring to FIGS. 1-2, 7 and 12, energy generated by the intraluminal generator 100 in response to the movement and/or deformation of the pressure change receiving structure 103 may be transmitted to an energy storage apparatus 105 operably coupled to the intraluminal generator 100 by an electrical coupling 106 (e.g. one or more wires).

Referring to FIGS. 1-2, 7 and 12, energy generated by the intraluminal generator 100 in response to the movement and/or deformation of the pressure change receiving structure 103 may be transmitted to an energy storage apparatus 105 operably coupled to the intraluminal generator 100 by an mechanical coupling 106 (e.g. one or more torque shaft, levers, piston, crankshaft and the like).

Referring to FIGS. 1-2, 7 and 12, energy generated by the intraluminal generator 100 in response to the movement and/or deformation of the pressure change receiving structure 103 may be transmitted to an energy storage apparatus 105 operably coupled to the intraluminal generator 100 by an fluid coupling 106 (e.g. a hydraulic line, pneumatic line, pipe, hose, and the like). One or more of the intraluminal generator 100 and the energy storage apparatus 105 may comprise a pump whereby energy may be transmitted via fluid flow (e.g. liquid or gas flow) between the intraluminal generator 100 and the energy storage apparatus 105.

Referring to FIGS. 1-2, 8 and 12, energy generated by the intraluminal generator 100 in response to the movement and/or deformation of the pressure change receiving structure 103 may be transmitted to an energy storage apparatus 105 operably coupled to the intraluminal generator 100 by an acoustical coupling 106. One or more of the intraluminal generator 100 and the energy storage apparatus 105 may comprise one or more of an acoustical transmitter (e.g. an acoustic transducer and the like) and an acoustical receiver (e.g. a hydrophone) whereby energy may be conveyed via acoustical signals transceived between the intraluminal generator 100 and the energy storage apparatus 105.

Further, the one or more acoustical transmitters and acoustical receivers may be in resonance (e.g. an acoustical transmitter generates acoustical waves that are in phase with a movement of the acoustical receiver).

Still further, the one or more acoustical transmitters and acoustical receivers may be in resonance (e.g. an acoustical transmitter generates acoustical waves that are in phase with a movement of the acoustical receiver) where the Q factor of the acoustical transmitter and acoustical receiver is at least 10,000. A transmitter/receiver device may be such as described in "Tunable high-Q surface-acoustic-wave resonator" by Dmitriev, et al., *Technical Physics*, Volume 52, Number 8, August 2007, pp. 1061-1067(7); U.S. Patent Application Publication No. 20060044078, "Capacitive Vertical Silicon Bulk Acoustic Resonator" to Ayazi, et al.; "Acoustic Wave Generation and Detection in Non-Piezoelectric High-Q Resonators", Lucklum, et al., *Ultrasonics Symposium*, 2006, October 2006, Pages: 1132-1135.

Referring to FIGS. 1-2, 9 and 12, energy generated by the intraluminal generator 100 in response to the movement and/or deformation of the pressure change receiving structure 103 may be transmitted to an energy storage apparatus 105 operably coupled to the intraluminal generator 100 by an electromagnetic radiation (EMR) coupling 106. One or more of the intraluminal generator 100 and the energy storage apparatus 105 may comprise one or more of an EMR transmitter and an EMR receiver whereby energy may be transmitted via EMR signals transceived between the intraluminal generator 100 and the energy storage apparatus 105.

Referring to FIGS. 1-2, 9 and 12, energy generated by the intraluminal generator 100 in response to the movement and/or deformation of the pressure change receiving structure 103 may be transmitted to an energy storage apparatus 105 operably coupled to the intraluminal generator 100 by an optical coupling 106. One or more of the intraluminal generator 100 and the energy storage apparatus 105 may comprise one or more of an optical transmitter (e.g. a light-emitting diode, a laser diode and the like) and an optical receiver (e.g. a photo diode, a photo detector and the like) whereby energy may be transmitted via optical signals transceived between the intraluminal generator 100 and the energy storage apparatus 105.

Referring to FIGS. 1-2, 9 and 12, energy generated by the intraluminal generator 100 in response to the movement and/or deformation of the pressure change receiving structure 103 may be transmitted to an energy storage apparatus 105 operably coupled to the intraluminal generator 100 by an infrared coupling 106. One or more of the intraluminal generator 100 and the energy storage apparatus 105 may comprise one or more of an infrared transmitter (e.g. a light-emitting diode, a laser diode and the like) and an optical receiver (e.g. a photo diode, a photo detector and the like) whereby energy may be transmitted via infrared signals transceived between the intraluminal generator 100 and the energy storage apparatus 105.

Referring to FIGS. 1-2, 10 and 12, energy generated by the intraluminal generator 100 in response to the movement and/or deformation of the pressure change receiving structure 103 may be transmitted to an energy storage apparatus 105 operably coupled to the intraluminal generator 100 by an inductive coupling 106. The intraluminal generator 100 may include circuitry (e.g. a solenoid) configured to generate a magnetic field. The energy storage apparatus 105 may include circuitry configured to generate an electrical current when disposed in a location proximate to the magnetic field.

Referring to FIGS. 1-2, 10 and 12, energy generated by the intraluminal generator 100 in response to the movement and/or deformation of the pressure change receiving structure 103 may be transmitted to an energy storage apparatus 105 operably coupled to the intraluminal generator 100 by a resonant inductive coupling 106. The intraluminal generator 100 and the energy storage apparatus 105 may include one or more waveguides configured to transceive evanescent electromagnetic signals. The waveguides may be configured such that a receiving waveguide is in resonance with a transmitting waveguide so as to provide evanescent wave coupling between the waveguides. Upon reception, the evanescent waves may be rectified into DC power for storage in the energy storage apparatus 105.

Further, a first intraluminal generator 100 and first energy storage apparatus 105 operably coupled by a first resonant inductive coupling 106 (as described above with respect to operation 1004) may be at least partially co-located with a second intraluminal generator 100 and second energy storage apparatus 105 operably coupled by a second resonant inductive coupling 106 within one or more anatomical structures. In order to avoid destructive interference between the first resonant inductive coupling 106 and the second inductive coupling 106, the waveguides associated with the first resonant inductive coupling 106 and the waveguides associated with the second inductive coupling 106 may be configured so as to be in mutual resonance.

Referring to FIGS. 1-2, 11 and 12, energy generated by the intraluminal generator 100 in response to the movement and/or deformation of the pressure change receiving structure 103 may be transmitted to an at least partially intraluminal energy storage apparatus 105 (e.g. energy storage apparatus 105) via a coupling 106.

Referring to FIGS. 1-2, 11 and 12, energy generated by the intraluminal generator 100 in response to the movement and/or deformation of the pressure change receiving structure 103 may be transmitted to an at least partially extraluminal energy storage apparatus 105 (e.g. energy storage apparatus 105B) via a coupling 106.

The herein described subject matter may illustrate different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, the convention (e.g., "a device having at least one of A, B, and C" would include but not be limited to devices that have A alone, B alone, C alone, A and B together, A and C together, B and C together, and/or A, B, and C together, etc.). In those instances where a convention analogous to "at least one of A, B, or C, etc." is used, in general such a construction is intended (e.g., "a device having at least one of A, B, or C" would include but not be limited to devices that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A device comprising:
an intraluminal piezoelectric generator including a deformable intraluminal pressure change-receiving structure, the deformable intraluminal pressure change-receiving structure (i) includes a piezoelectric material, (ii) includes a surface that is configured to be exposed to a fluid in a luminal environment, and (iii) is configured to generate electricity under deformation of the surface in response to receipt by the surface of a force from an intraluminal pressure change in the luminal environment;
an energy storage apparatus; and
a coupling between the intraluminal piezoelectric generator and the energy storage apparatus, wherein the coupling between the intraluminal piezoelectric generator and the energy storage apparatus comprises a fluid coupling.

2. A device comprising:
air intraluminal piezoelectric generator including a deformable intraluminal pressure change-receiving structure, the deformable intraluminal pressure change-receiving structure (i) includes a piezoelectric material, (ii) includes a surface that is configured to be exposed to a fluid in a luminal environment, and (iii) is configured to generate electricity under deformation of the surface in response to receipt by the surface of a force from an intraluminal pressure change in the luminal environment;
an energy storage apparatus; and
a coupling between the intraluminal piezoelectric generator and the energy storage apparatus, wherein the coupling between the intraluminal piezoelectric generator and the energy storage apparatus comprises an acoustical coupling.

3. A device comprising:
an intraluminal piezoelectric generator including a deformable intraluminal pressure change-receiving structure, the deformable intraluminal pressure change-receiving structure (i) includes a piezoelectric material, (ii) includes a surface that is configured to be exposed to a fluid in a luminal environment, and (iii) is configured to generate electricity under deformation of the surface in response to receipt by the surface of a force from an intraluminal pressure change in the luminal environment;
an energy storage apparatus; and
a coupling between the intraluminal piezoelectric generator and the energy storage apparatus selected from at least one of: a mechanical coupling, a fluid coupling, an acoustical coupling and an electromagnetic radiation coupling, wherein the coupling between the intraluminal piezoelectric generator and the energy storage apparatus comprises a coupling between the intraluminal piezoelectric generator and an at least partially extraluminal energy storage apparatus.

4. A system comprising:
means for converting an intraluminal pressure change into energy with an intraluminal piezoelectric generator including a deformable intraluminal pressure change-receiving structure, the deformable intraluminal pressure change-receiving structure (i) includes a piezoelectric material, (ii) includes a surface that is configured to be exposed to a fluid in a luminal environment, and (iii) is configured to generate electricity under deformation of the surface in response to receipt by the surface of a force from an intraluminal pressure change in the luminal environment;
means for providing the energy to an energy storage apparatus, wherein the means for providing the energy to an energy storage apparatus comprises means for providing the energy to an energy storage apparatus via a fluid coupling; and
means for storing the energy in an energy storage apparatus.

5. A system comprising:
means for converting an intraluminal pressure change into energy with an intraluminal piezoelectric generator including a deformable intraluminal pressure change-receiving structure, the deformable intraluminal pressure change-receiving structure (i) includes a piezoelectric material, (ii) includes a surface that is configured to be exposed to a fluid in as luminal environment, and (iii) is configured to generate electricity under deformation of the surface in response to receipt by the surface of a force from an intraluminal pressure change in the luminal environment;
means for providing the energy to an energy storage apparatus, wherein the means for providing the energy to an energy storage apparatus comprises means for providing the energy to an energy storage apparatus via an acoustical coupling; and
means for storing the energy in an energy storage apparatus.

6. A system comprising:
means for converting an intraluminal pressure change into energy with an intraluminal piezoelectric generator including a deformable intraluminal pressure change-receiving structure, the deformable intraluminal pressure change-receiving structure (i) includes a piezoelectric material, (ii) includes a surface that is configured to be exposed to a fluid in a luminal environment, and (iii) is configured to generate electricity under deformation of the surface in response to receipt by the surface of a force from an intraluminal pressure change in the luminal environment;

means for providing the energy to an energy storage apparatus wherein the means for providing the energy to an energy storage apparatus comprises: means for providing the energy to an at least partially extraluminal energy storage apparatus; and means for storing the energy in an energy storage apparatus.

* * * * *

UNITED STATES PATENT AND TRADEMARK OFFICE
CERTIFICATE OF CORRECTION

PATENT NO. : 9,526,418 B2  Page 1 of 1
APPLICATION NO. : 12/462789
DATED : December 27, 2016
INVENTOR(S) : Roderick A. Hyde et al.

It is certified that error appears in the above-identified patent and that said Letters Patent is hereby corrected as shown below:

Column 9, Line 52, Claim 2, "air intraluminal piezoelectric generator including a" should be --an intraluminal piezoelectric generator including a--

Signed and Sealed this
Fifth Day of September, 2017

Joseph Matal
*Performing the Functions and Duties of the*
*Under Secretary of Commerce for Intellectual Property and*
*Director of the United States Patent and Trademark Office*